(12) United States Patent
Leung et al.

(10) Patent No.: US 6,896,675 B2
(45) Date of Patent: May 24, 2005

(54) INTRADISCAL LESIONING DEVICE

(75) Inventors: Mark S Leung, Toronto (CA); Krishan Shah, Mississauga (CA); Frank H Baylis, Beaconsfield (CA)

(73) Assignee: Baylis Medical Company Inc., Montreal (CA)

( * ) Notice: Subject to any disclaimer, the term of this patent is extended or adjusted under 35 U.S.C. 154(b) by 0 days.

(21) Appl. No.: 10/087,856

(22) Filed: Mar. 5, 2002

(65) Prior Publication Data

US 2003/0171744 A1 Sep. 11, 2003

(51) Int. Cl.⁷ .............................................. A61B 18/18
(52) U.S. Cl. .......................................... 606/49; 607/96
(58) Field of Search ............................... 606/27–31, 47, 606/49; 607/96, 101, 108–112, 114

(56) References Cited

U.S. PATENT DOCUMENTS

| | | | |
|---|---|---|---|
| 2,973,762 A | 3/1961 | Koenig | |
| 3,848,281 A | 11/1974 | Mathews | |
| 4,369,788 A | 1/1983 | Goald | |
| 5,167,658 A | 12/1992 | Ensslin | |
| 5,201,729 A | 4/1993 | Hertzmann et al. | |
| 5,277,201 A | 1/1994 | Stern | |
| 5,366,491 A | 11/1994 | Ingram et al. | |
| 5,375,278 A | 12/1994 | Van Winkle et al. | |
| 5,433,739 A * | 7/1995 | Sluijter et al. ................. | 607/99 |
| 5,456,704 A * | 10/1995 | Kilcullen .................... | 607/111 |
| 5,584,086 A | 12/1996 | Van Winkle et al. | |
| 5,591,162 A * | 1/1997 | Fletcher et al. ............... | 606/25 |
| 5,630,961 A | 5/1997 | Salee | |
| 5,928,159 A * | 7/1999 | Eggers et al. ................ | 600/547 |
| 5,980,504 A | 11/1999 | Sharkey et al. | |
| 5,983,141 A | 11/1999 | Sluijter et al. | |
| 6,007,570 A | 12/1999 | Sharkey et al. | |
| 6,053,912 A * | 4/2000 | Panescu et al. ................ | 606/40 |
| 6,073,051 A | 6/2000 | Sharkey et al. | |
| 6,095,149 A | 8/2000 | Sharkey et al. | |
| 6,099,514 A | 8/2000 | Sharkey et al. | |
| 6,119,855 A * | 9/2000 | Yeager et al. ............ | 206/213.1 |
| 6,122,549 A | 9/2000 | Sharkey et al. | |
| 6,126,682 A | 10/2000 | Sharkey et al. | |
| 6,161,048 A | 12/2000 | Sluijter et al. | |
| 6,246,912 B1 | 6/2001 | Sluijter et al. | |
| 6,258,086 B1 | 7/2001 | Ashley et al. | |
| 6,259,952 B1 | 7/2001 | Sluijter et al. | |
| 6,261,311 B1 | 7/2001 | Sharkey et al. | |
| 6,264,650 B1 | 7/2001 | Hovda et al. | |
| 6,283,960 B1 | 9/2001 | Ashley | |
| 6,290,715 B1 | 9/2001 | Sharkey et al. | |
| 6,575,969 B1 * | 6/2003 | Rittman et al. ................ | 606/41 |
| 2001/0001314 A1 | 5/2001 | Woloszko et al. | |
| 2004/0064137 A1 | 4/2004 | Pellegrino et al. | |

FOREIGN PATENT DOCUMENTS

| | | |
|---|---|---|
| EP | 0 438 242 A | 7/1991 |
| EP | 1 402 838 A1 | 3/2004 |
| WO | WO-98/17190 A3 | 4/1998 |
| WO | WO-99/47058 A3 | 9/1999 |
| WO | WO-01/45579 A1 | 6/2001 |
| WO | WO-01/62168 A2 | 8/2001 |

OTHER PUBLICATIONS http://www.orthoassociates.com/IDET.htm, Jun. 11, 2000, 5 pages.

(Continued)

*Primary Examiner*—Roy D. Gibson
*Assistant Examiner*—Aaron Roane
(74) *Attorney, Agent, or Firm*—Ogilvy Renault

(57) ABSTRACT

An intradiscal device for treatment of a patient's intervertebral disc. The device has two elongate probes for insertion to two spaced apart treatment sites of the annulus fibrosus. The distal portions of each probe have energy delivery means for delivering energy between the distal portions of the probes through the annulus fibrosus adjacent the two treatment sites. The energy is preferably electrical energy the probes may be inserted surgically through respective elongate introducer tubes.

20 Claims, 8 Drawing Sheets

OTHER PUBLICATIONS

Derby, R., Eek, B., Chen, Y., O'Neill, C., Ryan, D., Intradiscal Electrothermal Annuloplasty (IDET): A Novel Approach for Treating Chronic Discogenic Back Pain. *Neuromodulation.* 2000, 3(2), 82–88.

Saal, Joel, Saal, Jeffrey, Management of Chronic Discogenic Low Back Pain with a Thermal Intradiscal Catheter. *Spine.* 2000, 25(3), 382–388.

Wiesel S. W., Sharp Criticism of Intradiscal Thermal Therapy Research. *The Back Letter.* 2000, 15(6), 61–64. Lippincott Williams & Wilkins, 1 page.

Wiesel S. W., IDET: Is There Any Indication That Intradiscal Thermal Therapy Works? *The Back Letter.* 2000, 15(6), 64–65. Lippincott Williams & Wilkins, 3 pages.

IDET Reference Literature List, Jun. 15, 2000, Oratec Interventions Inc., Doc. # 770023 Rev 05, 7 pages.

Abstract: Arthroscopic Electro–Thermal Surgery for Discogenic Low Back Pain: A Preliminary Report. May 28, 1998, 1 page.

Press Release: SPINE Journal Studies Support Oratec's IDET Back Pain Treatment Two Peer Reviewed Articles Report Substantial Reduction in Pain. Oratec, Oct. 19, 2000, 1 page.

510(k) Summary: SpineCATH Mar. 19, 1998 and Document # K974464, Jan. 23, 1998, 8 pages.

510(k) Summary: SpineCATH, Dec. 17, 1999, Document # K993967, 4 pages.

Yahoo News Re: Oratec Dec. 20, 2000, Jan. 8, 2001, Jan. 25, 2001, Mar. 2, 2001, 6 pages.

510(k) Summary: Radionics Disc Catheter Electrode System, Document K001741, Oct. 23, 2000, 5 pages.

SpineCATH Intradiscal Catheters by Oratec, Instructions for Use, Document No. 700242, Rev. 03, .

Radionics RF Lesioning Systems and RF Catheter Electrode System Photo.

SPINE vol. 21, No. 15, HOUPT, Jonathan C. et al. Experimental Study of Temperature Distributions and Thermal Transport During Radiofrequency Current Therapy of the Intervertebral Disc. pp. 1808–1813, 1996, Lippincott–Raven Publishers by J.C. Houpt, S. Conner, E. McFarland.

Nerve Ingrowth Into Diseased Intervertebral Disc in Chronic Back Pain, A.J. Freement, T.E. Peacock, P. Goupille, J.A. Hoyland, J. O'Brian, M.I.V. Jayson, The Lancet, pp. 178–181, 1997.

Michael Karasek, MD, and Nikolai Bogduk, MD, PhD, DSct, "Twelve–Month Follow–Up of a Controlled Trial of Intradiscal Thermal Anuloplasty for Back Pain Due to Internal Disc Disruption", Reprinted from Spine, vol. 25, No. 20, Oct. 2000, Lippincott Williams & Wilkins, pp. 2601–2607.

Jeffrey A. Saal, MD, and Joel S. Saal, MD, "Intradiscal Electrothermal Therapy for the Treatment of Chronic Discogenic Low Back Pain", Operative Techniques in Orthopaedics, vol. 10, No. 4, Oct. 2000, pp. 271–281.

IDET Reference Literature List with abstracts, Mar. 15, 2001, Oratec Interventions Inc., 77 0023, Rev. 09, pp. 1–5.

IDET Procedure with SpineCATH, Dec. 2000, Oratec Interventions Inc., 77 0004, Rev. 4, pp. 1–6.

Material Safety Data Sheet for LITE–DRI® Absorbent (MSD–006) for the New Pig Corporation, Tipton, PA., pp. 1 & 2.

http://www.newpig.com/Npdoc/browse/pp.ihtml?productld=PLP201, PIG® Lite–Dri® Absorbent, entitled LITE–DRI® Absorbent absorbs 3 times more than clay!.

http://ww.jm.com/insulation/faqs res/019.html, JM FAQ—entitled "What are the differences (pros and cons) between fiber glass and cellulose insulation?".

http://ww . . . /ppDocPage.jhtm;?url=%2FNPdoc%2Fcontent%2F1587345%2FPLP201.ht.New Pig Leak & Spill Absorbents, entitled Product Data Sheet.

http://www.ianr.unl.edu/pubs/housing/nf40.htm, Insulation Information for Nebraska Homeowners, NF 91–40, entitled "Insulation Information for Nebraska Homeowners".

Zanders USA, Bulletin 2, entitled "Ambient Control and Paper Stability", pp. 5–7.

* cited by examiner

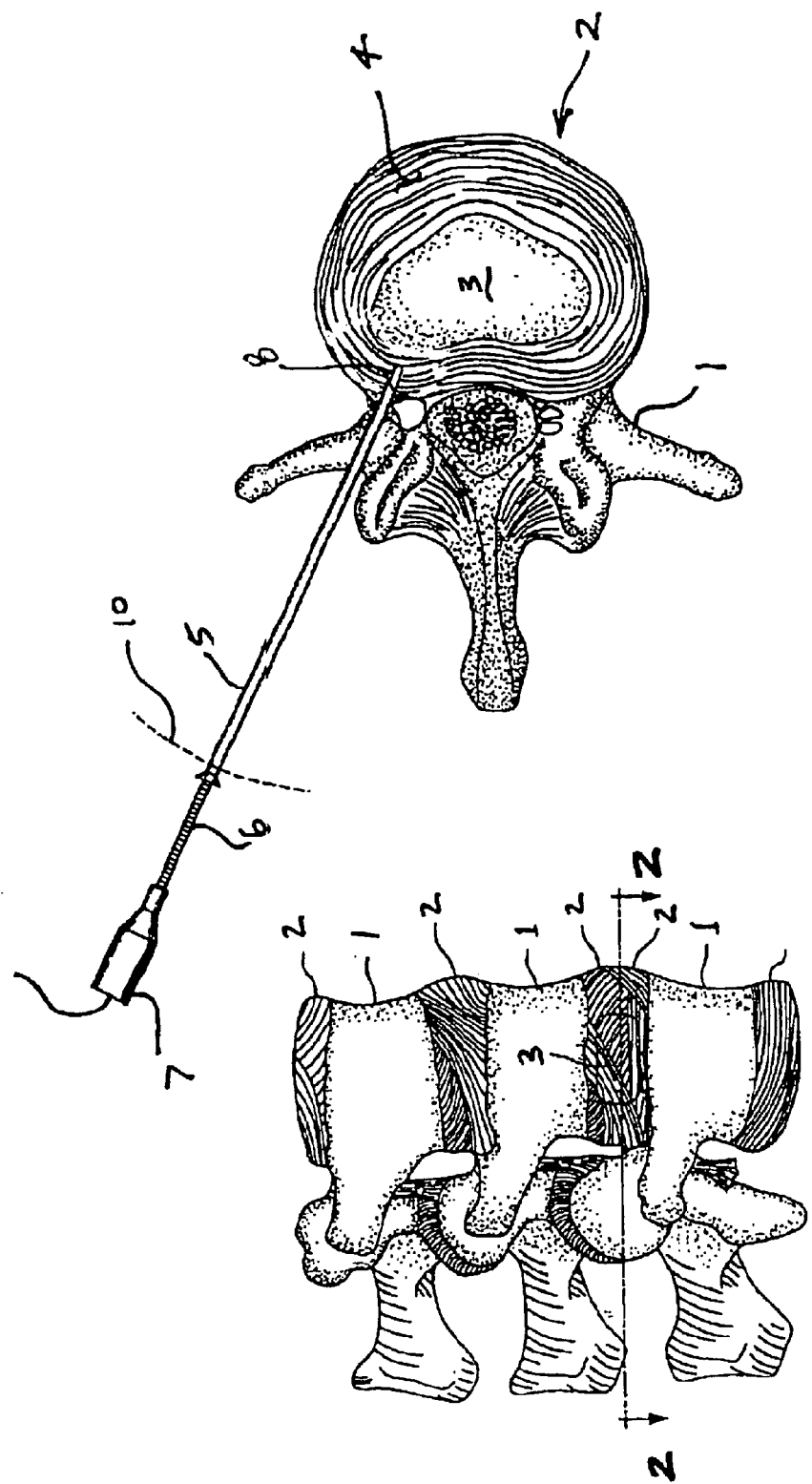

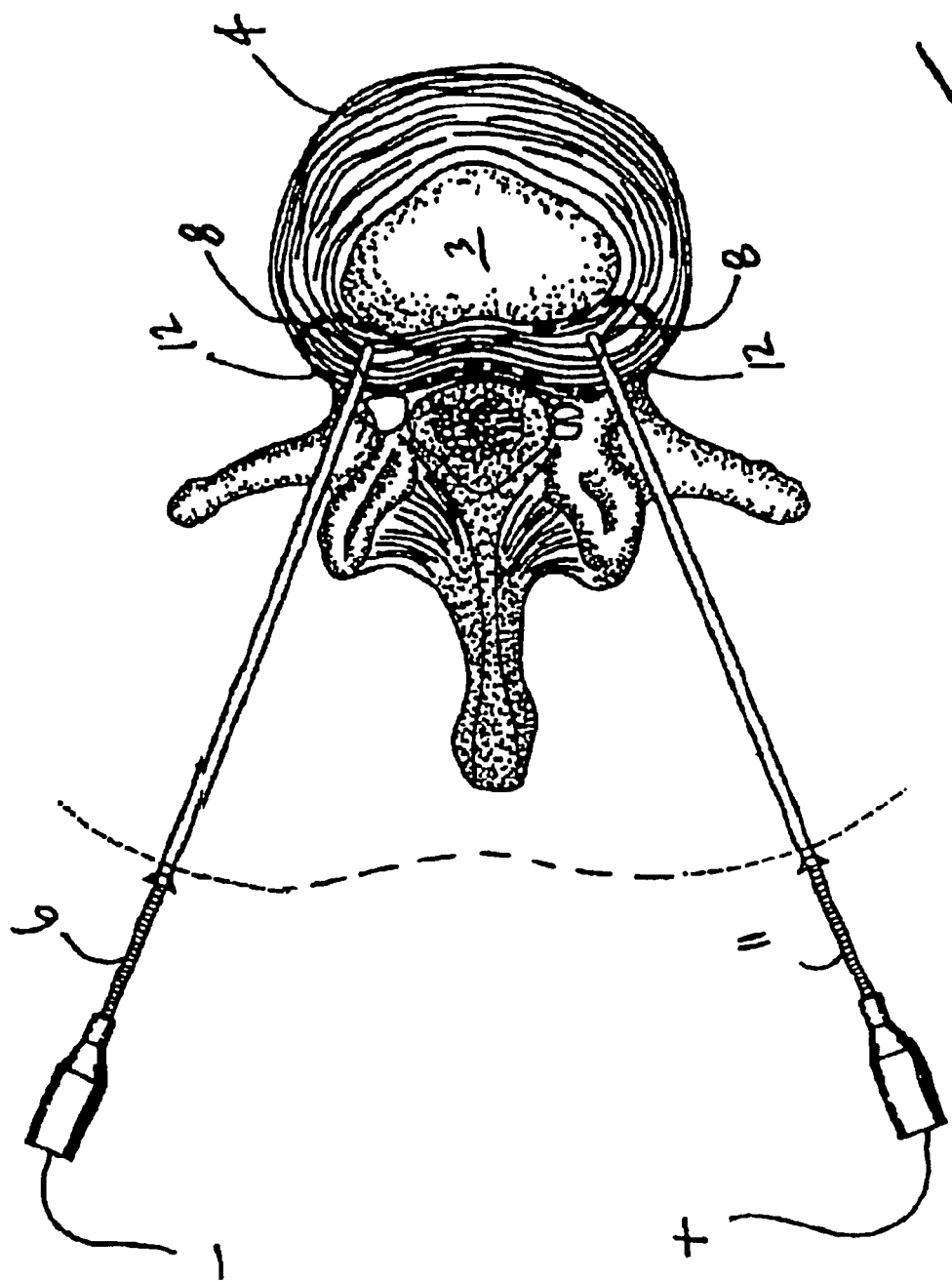

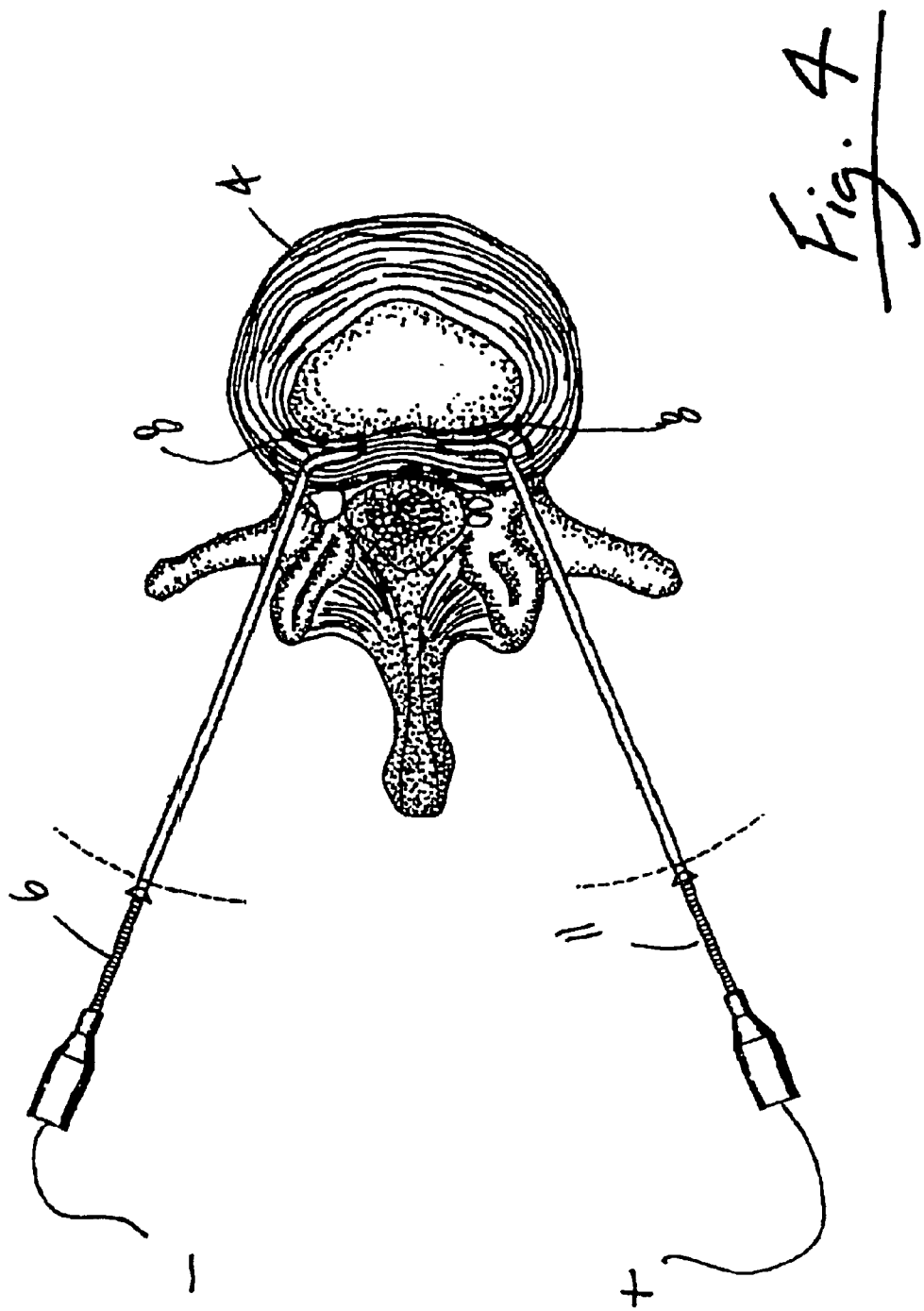

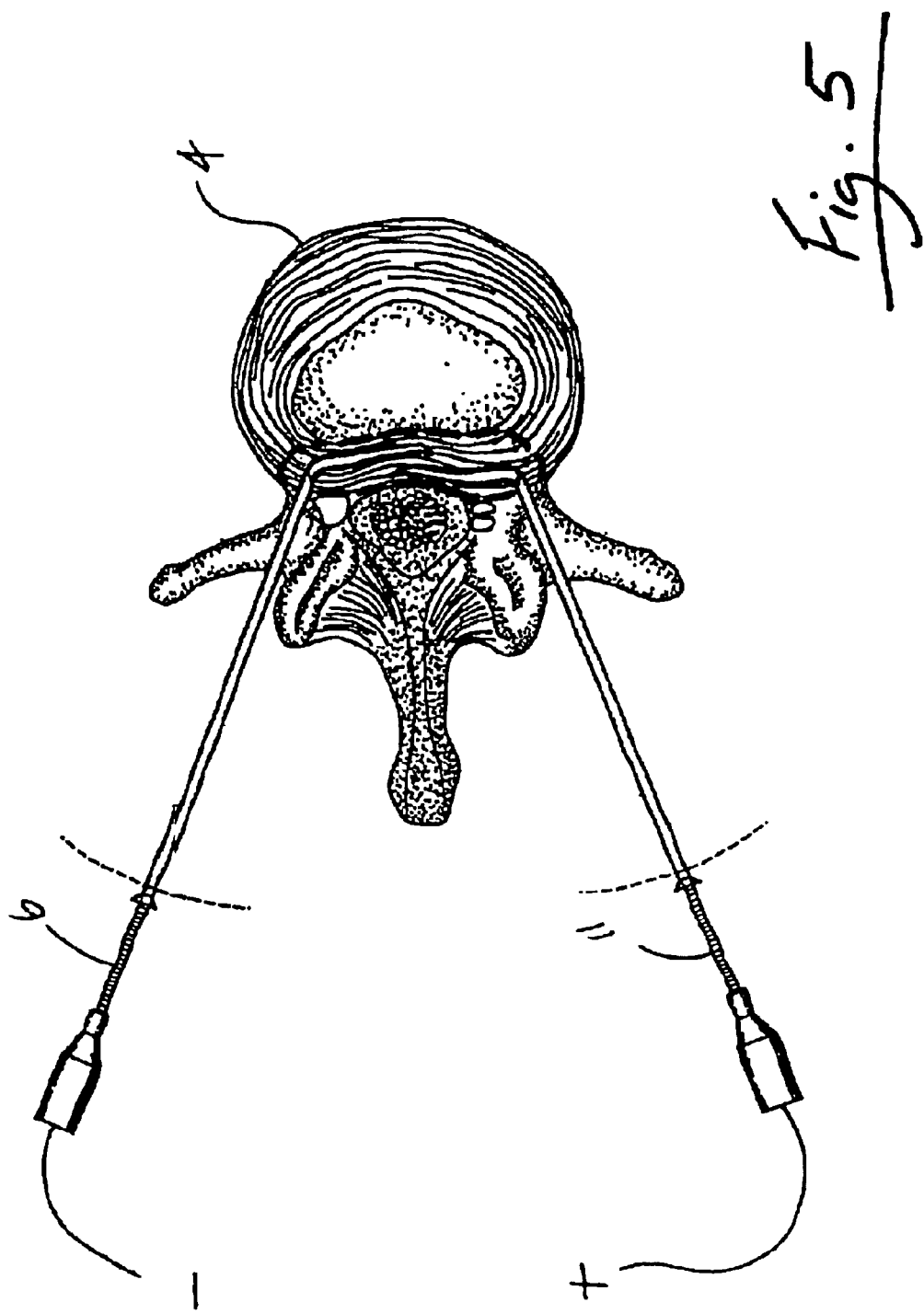

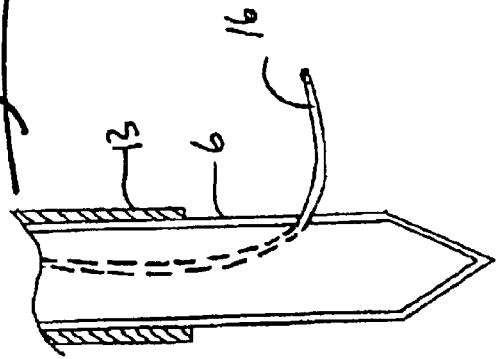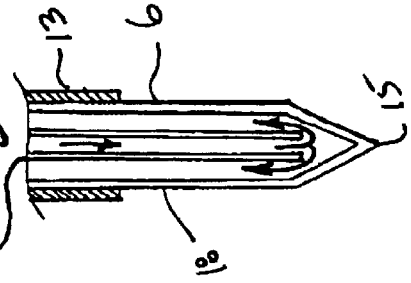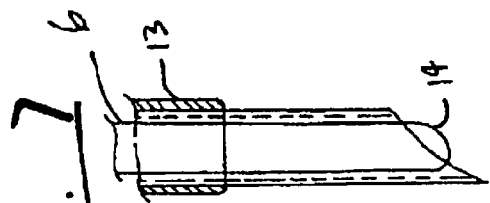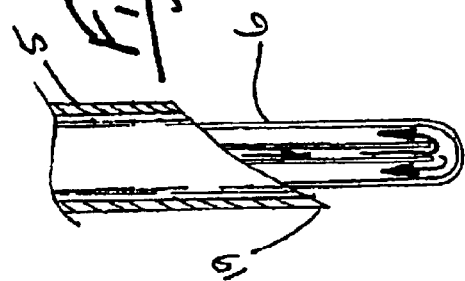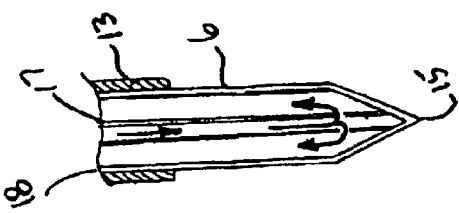

INTRADISCAL LESIONING DEVICE

TECHNICAL FIELD

The invention relates to a method and apparatus for applying energy, particularly radio frequency electrical energy, to a region of the annulus fibrosis of an intervertebral disc in treatment of intervertebral disc disorders using two percutaneous probes.

BACKGROUND OF THE ART

The human intervertebral junction is characterized principally by an intervertebral disc interposed between adjacent vertebral surfaces. The size and configuration of discs vary between the six discs of the cervical region, the twelve discs of the thoracic region, six of the lumbar region and one disc between the sacrum and coccyx.

Intervertebral discs are neither homogeneous nor static. Changes to a disc can affect the vertebral column activity significantly. The intervertebral disc is a complex structure where its dynamic properties result from the interaction of a central, gelatinous nucleus pulposus encircled by a tough, fibrous, semielastic annulus fibrosus. Further, thin cartilage endplates and vertebral body ring apophyseal attachments of the annulus fibrosus join the disc to the vertebrae craniad and caudad to the disc. Although the nucleus pulposus is gelatinous and somewhat fluid while the annulus fibrosus comprises circularly arranged fibers, the border between these components is not distinct in a healthy adult disc. Any distinction is less apparent in a damaged disc where tissues are intermingled in a gradual transition layer.

The annulus fibrosus is composed of concentric layers of fibrocartilage, in which collagen fibers are arranged in parallel strands running obliquely between vertebral bodies. The inclination is reversed in alternate layers thereby crossing over each other obliquely. In children and adolescents, the nucleus pulposus is an amorphous colloidal mass of gelatinous material containing glycosaminoglycans, collagen fibrils, mineral salt, water and cellular elements. The nucleus pulposus has an important function in nutrition of the disc and contributes to the mechanical ability of the disc to act as a shock absorber and allow flexibility. The nucleus pulposus is normally under pressure and is contained within an ovoid cavity formed laterally by the annulus fibrosus and bounded by thin plates of hyaline cartilage endplates covering the adjacent vertebrae.

The intervertebral discs form about one-quarter the length of the vertebral column in a healthy adult human. Discs are thickest in the cervical and lumbar regions, where the movements of the vertebral column are greatest. The vertebral column, including the intervertebral discs, undergo various morphological and biochemical changes over time, such as dehydration of the discs and concaving vertebral bodies. As a result, the size and configuration of the disc components vary considerably from person to person.

Lower back injuries and chronic back pain are a major health problem resulting not only in a debilitating condition for the patient, but also in consuming a large proportion of funds allocated for health care, social assistance and disability programs. Disc abnormalities and pain may result from trauma, repetitive use in the workplace, metabolic disorders, inherited proclivity or aging. The existence of adjacent nerve structures and innervation of the disc are very important issues in respect to patient treatment for back pain.

Common disorders of the intervertebral disc include localized tears or fissures in the annulus fibrosus; disc herniations with contained or escaped extrusions of the nucleus pulposus; and chronic circumferential bulging of discs. For most patients, however, a well-defined abnormality cannot be found to solely explain the cause of the low back pain, making treatment and pain management very difficult. Since isolating a specific anatomic disorder as the sole cause of pain is rare, most patients are merely treated symptomatically to reduce pain, rather than receiving treatment to eliminate the cause of the condition.

One course of pain may be attributed to the structure of the annulus fibrosus. The annulus fibrosus is thinner nearer to the posterior than to the anterior margin of the disc, and many disc ruptures occur in the posterior region thereby exerting pressure on the adjacent nerve fibers causing pain. The pain experienced by the disc exerting pressure on the adjacent nerves is characterized by referred pain, or pain felt predominantly elsewhere in the body where the affected nerve travels. A common example of this is sciatica where an intervertebral disc exerts pressure on the sciatic nerve.

Another cause of pain resulting from disc pathology is chemically induced pain. The nucleus pulposus contains chemicals that may induce pain if contact is made with certain nerve structures. If an intervertebral disc is herniated severely enough that a portion of the nucleus pulposus is extruded from the disc, and the portion comes in contact with an adjacent nerve, chemically induced pain can be felt. This is also a cause of sciatica.

Increasingly, evidence suggests that the source of back pain in many patients is a result of nerves within the degenerated disc itself or nerves that have grown into the disc in concordance with disc injury. For example, as documented by Jonathan C. Houpt, BA, Edison S. Conner, MD, and Eric W. McFarland in "Experimental Study of Temperature Distributions and Thermal Transport During Radio frequency Current Therapy of the Intervertebral Disc", Spine. 1996; 21(15), 1808–1813, afferent innervation of the outer half of the annulus fibrosus has been established whereas the nucleus pulposus contains no nerves or blood vessels. Pain response has been widely reported in response to specific stimulation of the outer layers of the annulus fibrosus. In another study documented by A. J. Freemont, "Nerve ingrowth into diseased intervertebral disc in chronic back pain", The Lancet. 1997; 350, 178–181, nociceptive nerves were found ingrown deeper into the disc, as far as the nucleus pulposus, in association with disc degeneration. The pain experienced from nerves in a damaged intervertebral disc is more localized to the spine. The stimulation can be both mechanical and chemical. Some patients may feel a combination of back pain and referred pain indicating that pain is being transmitted both from nerves in the disc and from impinged nerves adjacent to the disc.

Where patients are diagnosed with clear chronic discogenic pain (i.e. pain originating from a disc), complete surgical removal of the intervertebral disc (called discectomy) and fusion of the adjacent vertebrae is often carried out with success rates over 80% in measurable pain reduction after surgery. Such major surgical procedures are highly invasive, expensive and involve significant risk. Furthermore motion is impeded once the vertebrae are fused and there may be adverse mechanical effects on the adjacent remaining discs.

To alleviate some of the disadvantages of open-surgery discectomy, percutaneous methods of removing the disc or part of the disc have been practiced. Methods that remove part of the nucleus pulposus are designed to decrease the volume in order to reduce internal disc pressure thus reducing external pressure exerted on adjacent nerves. Examples of such methods that include mechanical means can be found in, for example, U.S. Pat. No. 4,369,788 to Goald that describes the use of a mechanical device for use in microlumbar discectomy, and in U.S. Pat. No. 5,201,729 to Hertzmann et al. that describes a percutaneous method of discectomy using a laser. Other methods of removing the disc or part of the disc include chemically dissolving the nucleus pulposus using the enzyme Chymopapain. U.S. Pat. No. 6,264,650 to Hovda et al. describes a method of vaporizing a portion of the nucleus pulposus using radio frequency electrical current. These prior art methods have shown variable success and there are several advantages of percutaneous procedures over open surgical discectomy and vertebral fusion including less trauma to the patient, preserved spinal movement, less disruptive effect on adjacent discs, less risk of infection and less risk of accidental injury. However, these methods cause damage to the nucleus pulposus, which is essential to the maintenance of the disc. Further, the damaged annulus fibrosus is not treated.

Due to the pain reduction success of surgical discectomy, less drastic means of denervating rather than surgically removing the disc are of significant interest. To denervate is to intervene with the transmission of a sensory signal in a nerve. A denervated disc does not cause discogenic pain and the disc is left intact to preserve its mechanical function. Denervating the disc especially by using percutaneous probes is much less invasive, less costly and less risky. The procedure is also simpler to administer and does not require the fusing of adjacent vertebrae thereby better preserving the patient's freedom of movement.

To destroy nerve cells in the annulus fibrosus, the prior art includes probes that emit various forms of energy from within the nucleus pulposus such as, radio frequency electric current, microwave or thermal energy. It appears that the disc is devoid of temperature sensing neurological structures, probably since the disc is at core body temperature, and only mechanical and chemical stimulus-sensing nociceptors exist in the annulus fibrosus.

U.S. Pat. No. 5,433,739 to Sluijter et al. describes a method of relieving back pain through percutaneous insertion of a needle or electrode into the center of the intervertebral disc within the nucleus pulposus under fluoroscopy or other imaging control. The U.S. Pat. No. 5,433,739 patent describes the heating of the outer layers of the annulus fibrosus to a temperature that is lethal to the nerve structures thereby denervating the disc to relieve discogenic pain. The temperature of the tissue is increased by applying high frequency electric current through the tissue.

Radio frequency electrodes including an insulated shaft with an exposed tip conducting radio frequency current are commonly used in neurosurgery, anesthesiology and cardiology to lesion neural tissue. A second dispersive electrode with large surface area is placed elsewhere on the patient's body surface to complete the circuit. The intensity of radio frequency current at the exposed tip causes heating of the adjacent tissue. When the temperature increases sufficiently, the tissue is coagulated. The temperature that is sufficient to coagulate small unmyelinated nerve structures is 45° C., at which point direct interruption of the nerves occurs by the formation of a lesion. Thus, the transmissions of pain signals are blocked.

It is well known to those skilled in the art that percutaneous access to an intervertebral lumbar disc involves either a posterolateral approach or an anterior approach. The anterior approach is more invasive than the posterolateral approach because of the organs in the abdominal and pelvic cavities. The most common percutaneous approach to the lumbar disc, to those skilled in the art, is to insert a needle or tube posterolateral to the disc, just lateral of the zygapophyseal joint, inferior to the spinal nerve and into the posterolateral region of the annulus fibrosus.

In accordance with U.S. Pat. Nos. 5,980,504; 6,007,570; 6,073,051; 6,095,149; 6,099,514; 6,122,549; 6,126,682; 6,258,086 B1; 6,261,311 B1; 6,283,960 B1; and 6,290,715 B1 to Sharkey et al. to permit percutaneous access to the posterior half of the nucleus or to the posterior inner wall of the disc, a flexible heating element may be inserted into the nucleus pulposus through a hollow tube that has been pierced through the annulus fibrosus. The flexible heating element has sufficient rigidity to be advanced longitudinally under force through the nucleus pulposus while having flexibility to be compliant to the inner wall of the annulus fibrosus. The heating element is guided by sliding contact with the inner wall and ideally should not puncture or damage the annulus fibrosus during positioning. Another embodiment of the U.S. Pat. No. 6,258,086 B1 patent is a flexible probe that contains an activation element on the distal portion that changes the shape of the probe once it is in the nucleus pulposus. According to the Sharkey et al. patents, the flexible heating elements operate to denervate the outer layers of the annulus fibrosus as well as modulate the collagen in the annulus fibrosus by applying heat. Raising the temperature above about 60° C. will break structural bonds of collagen fibers causing them to contract and tighten. This collagen tightening effect is lost once the temperature of the collagen is raised above about 75° C. where the fibers loosen, resulting in zero net volume change.

It is also known to insert an energy delivery device in to the nucleus pulposus, or the transition zone between the nucleus pulposus and the inner wall of the annulus fibrosus, in order to transfer heat from the nucleus pulposus to selected areas of the annulus fibrosus. These known methods do not allow applying energy to these target areas without unnecessarily entering and applying energy to the nucleus pulposus.

There are several disadvantages to unnecessarily entering into and applying energy to the nucleus pulposus. Disadvantages include disrupting the metabolism of the intervertebral disc, impeding the healing processes, and altering the structure of healthy tissues of the disc such as the cartilage endplates, nucleus pulposus and areas of the annulus fibrosus that are not targeted. Additional disadvantages include causing unnecessary physical damage, increasing the risk of discitis, and potentially removing nuclear material that can come in contact with other adjacent tissues thus causing biochemical damage. If energy is applied to the target areas of the intervertebral disc without inserting a device into the nucleus pulposus, these disadvantages are avoided.

It has also been found that the nucleus pulposus has very high heat conductivity probably due to its gelatinous and high water content characteristics. The manipulation of prior art probes within the nucleus pulposus to position an energy emitter close to the site of the annulus injury appears to be largely unnecessary since heat is readily conducted throughout the nucleus pulposus no matter where the probe is located within the nucleus. Clearly the prior art is less than optimal since these techniques involve damage to the annulus fibrosus which is pierced to gain access to the nucleus pulposus. Even once disposed within the nucleus pulposus, the delivery of sufficient energy to denervate the desired area is inhibited by dissipation caused by the high heat conductivity of the nucleus pulposus. Using the methods described in the prior art the annulus is punctured thus spreading heat to all parts of the nucleus pulposus.

Another prior art device, described in PCT publication number WO 01/45579 to Finch et al., avoids entry into the nucleus pulposus by extending a probe a relatively long distance within the annulus fibrosus conforming to an azimuthal course defined by the natural lamina of the annulus fibrosus. Therefore the elongate probe extends between layers of the annulus fibrosus to deliver heat energy to a large segment of the annulus fibrosus without entering the nucleus pulposus or directly heating the nucleus itself. However, tunneling through the layers of the annulus fibrosus can significantly damage the annulus fibrosus and layers may peel apart. Surgical manipulation involves inaccuracies and in the case of ruptured or fissured discs, tunneling may cause further deterioration of the annulus fibrosus.

There is interest among researchers that the application of high frequency current without a rise in temperature alters nerve function to relieve pain and also may cause collagen production to increase and stimulate healing of the annulus fibrosus. The use of high frequency current without heating to relieve pain by modifying neural tissue is described in U.S. Pat. Nos. 5,983,141; 6,161,048; 6,246,912; and 6,259,952 to Sluijter et al. These patents describe the use of a modified signal wave that includes rest periods to allow heat to dissipate. The modified high frequency signal is applied to the patient using a single active electrode and a ground electrode attached to the skin of the patient. These prior art patents ('141, '048, '912, and '952) do not discuss using high frequency current to increase collagen production nor do they discuss this application in the intervertebral disc. The prior art inventions that are specifically designed for treatment of intervertebral discs (Sharkey et al. U.S. Pat. Nos. 5,980,504; 6,007,570; 6,073,051; 6,095,149; 6,099,514; 6,122,549; 6,126,682; 6,258,086 B1; 6,261,311 B1; 6,283,960 B1; and 6,290,715 B1; Sluijter et al. U.S. Pat. No. 5,433,739; Finch PCT publication number WO 01/45579) do not discuss the application of high frequency current without a rise in temperature to alter nerve function to relieve pain or to cause collagen production to increase. The advantages of non-thermal application of high frequency electrical current to treat intervertebral discs include reduced risk of thermal damage, increased production of collagen to strengthen the annulus fibrosus, and reduced discogenic pain while stimulating the healing processes.

It is an object of the present invention to provide a device that can treat intervertebral disc disorders by applying energy to the injured or degenerated areas of the annulus fibrosus, without the need to tunnel through or otherwise severely damage the annulus fibrosus and without the need to enter into or heat the nucleus pulposus.

It is a further object of the present invention to deliver energy to a relatively large elongate segment of the annulus fibrosus without the need to physically insert a probe into the entire segment thereby avoiding the risk of further deteriorating the treated segment of the annulus fibrosus.

Further objects of the invention will be apparent from review of the disclosure, drawings and description of the invention below.

SUMMARY OF THE INVENTION

The invention provides an intradiscal lesioning device for percutaneous treatment of a patient's intervertebral disc.

In one aspect, the invention provides an intradiscal lesioning device for percutaneous treatment of a patient's intervertebral disc including a nucleus pulposus bounded by an annulus fibrosus. The device comprises a first and a second elongate probe for surgical insertion to two spaced apart treatment sites of the annulus fibrosus. Each probe has a proximal portion and a distal portion. The distal portion of each probe comprises an energy delivery means for delivering energy between the distal portions of the probes, through the annulus fibrosus adjacent and between the two treatment sites.

The device can also have two elongate introducer tubes each having an inner end, an outer end and a longitudinal hollow bore extending therebetween, for percutaneous surgical insertion to two spaced apart treatment sites of the annulus fibrosus thereby providing external surgical access to the annulus fibrosus through each bore. The elongate probes are longitudinally inserted through the bore from the inner to the outer end of the introducer tube. The distal portions of each probe energy delivery means for delivering energy between opposing distal portions of the probes through the annulus fibrosus adjacent the two treatment sites, for denervating and stiffening the annulus fibrosus. Preferably the energy is electrical current having a frequency within the radio frequency range or at least above physiological stimulation range. Since the annulus fibrosus has an impedance less than the tissue surrounding the disc, the device can also include an electrical current impedance meter communicating between the distal portions of each probe to determine the position of the electrodes, determine whether cracks or fissures are present in the annulus fibrosus which increase impedance and to determine the optimal level of power needed to effectively treat the section of the annulus fibrosus.

In a further aspect, the present invention provides a method for the treatment of an intervertebral disc including a nucleus pulposus bounded by an annulus fibrosus. The method comprises the steps of inserting a first and a second intradiscal lesioning probe into the annulus fibrosus, each probe having an energy delivery means located at a distal end thereof, the distal ends being spaced apart when inserted and delivering energy from an energy source through the energy delivery means to the annulus fibrosus.

DESCRIPTION OF THE DRAWINGS

In order that the invention may be readily understood, embodiments of the invention are illustrated by way of examples in the accompanying drawings, in which:

FIG. 1 is lateral view of a portion of a human spine with three vertebra divided by intervertebral discs showing the location of the nucleus pulposus in dashed outline surrounded by overlapping layers of the annulus fibrosus;

FIG. 2 is a sectional view along lines 2—2 of FIG. 1 showing the laminar characteristic of the annulus fibrosus with a first probe in a catheter tube embedded within the annulus fibrosus;

FIG. 3 is a like sectional view showing two probes embedded within the posterior region of the annulus fibrosus to treat an elongate area by passing electrical current between the distal ends of the spaced apart probes;

FIG. 4 shows an alternative sectional view where the probes have been inserted laterally into the laminar structure of the annulus fibrosus to extend the treatment area as electrical current is passed between the distal ends of the probes;

FIG. 5 is another like view showing the probes extended laterally into the posterior region of the annulus fibrosus again effecting the shape of the area of treatment;

FIG. 7 is a detailed sectional view of a radio frequency delivery probe containing a temperature sensor inserted into an insulated cannula with a bare tip;

FIG. 8 is a detailed sectional view of a liquid-cooled electrode;

FIG. 9 is a view of a liquid-cooled high frequency electrode with a remote reaching temperature sensor;

FIG. 10 is another alternative view of a liquid-cooled electrode;

FIG. 11 is an alternative view of a liquid-cooled electrode that is inserted through an introducing catheter;

Figure 6:
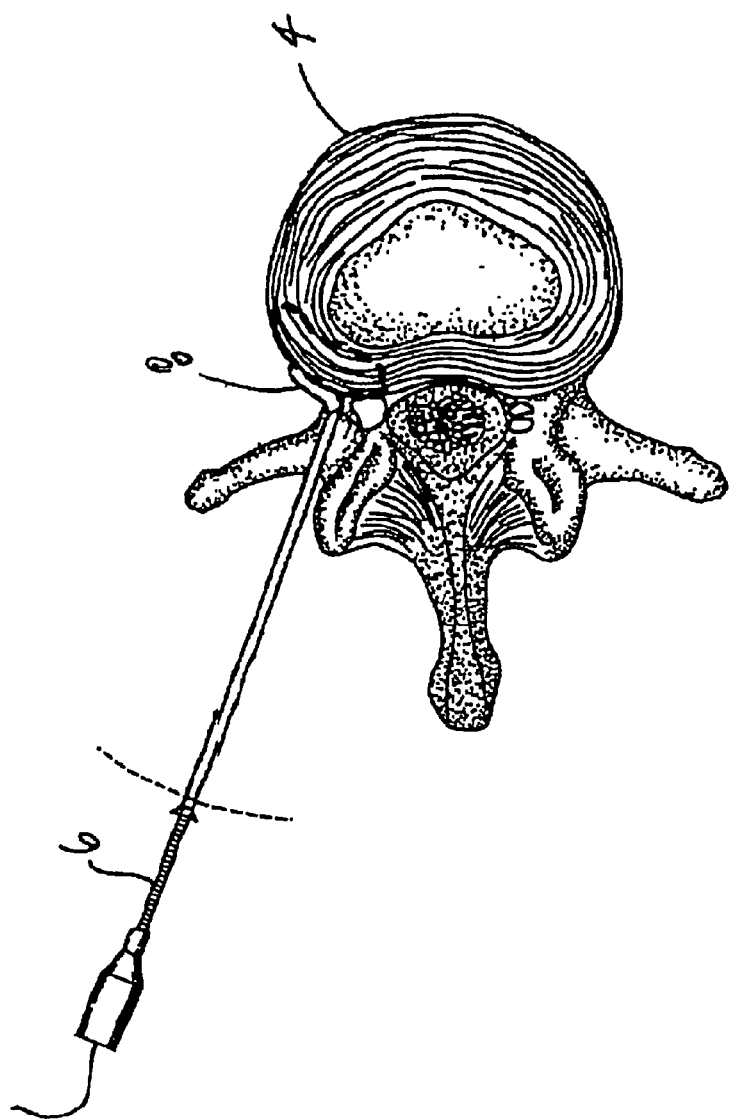
FIG. 6 shows a similar sectional view with the first probe extended laterally to contact an external surface of the annulus fibrosus without piercing or damaging the annulus fibrosus further.

Further details of the invention and its advantages will be apparent from the detailed description included below.

DETAILED DESCRIPTION OF THE INVENTION

FIGS. 1 and 2 illustrate a section of a patient's vertebrae 1 and a typical uninjured intervertebral disc 2. The centrally located nucleus pulposus 3 is bounded by the annulus fibrosus 4 and the cartilage endplates (not shown). The cartilage endplates are joined to the vertebrae above and below the intervertebral discs. Metabolites diffuse from blood vessels in the vertebrae 1 through the cartilage endplates to the nucleus pulposus 3 and annulus fibrosus 4. FIG. 2 shows one embodiment of a first probe 6 is inserted through an introducer tube 5, also referred to as a catheter tube. The proximal portion 7 of probe 6 is connected to an electrical power source (not shown). In the embodiment shown in FIG. 2, the distal portion 8 of the probe 6 is inserted partially into the annulus fibrosus 4 to conduct electrical current or apply heat thereto as further described with reference to FIG. 3.

Although some of the figures and the description relate to the percutaneous insertion of the probes into the annulus fibrosus it will be understood that the probes can also be used during surgery and can be inserted directly into the annulus fibrosus through an open cavity.

FIG. 3 shows the percutaneous surgical insertion of a second elongate probe 11 as well as first elongate probe 6 that are each extended to penetrate the annulus fibrosus 4 at two spaced apart treatment sites 12. The distal portions 8 of each probe 6 and 11 include an energy delivery means for delivering energy between the distal portions 8 of the probes 6 and 11 through the annulus fibrosus 4 adjacent to the two treatment sites 12. In this context the use of the term adjacent is not limited to meaning the delivery of energy to the tissue touching the probe or in the immediate vicinity of the probe but extends to incorporate the delivery of energy to tissue that is surrounding the probes and particularly tissue located between the probes. Preferably, the energy delivery means is an electrode and the electrical current conducted between the probes 6 and 11 has a frequency within the radio frequency range. Other forms of energy can be used including microwave, ultrasound and thermal energy.

FIG. 4 shows approximately the same view as FIG. 3 except with the distal ends 8 of the probes 6 and 11 extended laterally into the annulus fibrosus 4 to more effectively cover the treatment area indicated in dashed outline. As mentioned above, the most common location for disc injuries is relatively inaccessible in the posterior region. Therefore extending the distal ends 8 as indicated in FIGS. 4 and 5 provides the ability to deliver electrical current in a relatively small focussed area.

FIG. 5 shows a further extension of the distal ends 8 within the annulus fibrosus 4 indicating how the directional shape control of the probe tips 8 can be used to pinpoint the damaged area of the disc.

FIG. 6 shows a further example of deployment of probe 6 where the annulus fibrosus 4 is not punctured but rather the tip 8 of the probe 6 is directed to contact the external surface of the annular fibrosus 4 only. Preferably, probe 11 (not shown) is positioned to concentrate energy at a desired elongate location, as shown in dashed outline.

The use of two electrode probes 6 and 11 provides treatment for the area of the annulus fibrosus 4 between the tips 8 of the probes 6 and 11 when electrical current is passed between the tips through the annulus fibrosus 4. The relatively low impedance of the annulus fibrosus 4 compared to surrounding tissues ensures that electrical energy is not rapidly dissipated but remains focussed in the area bounded by the two electrode tips 8. As mentioned above, the annulus fibrosus has electrical impedance characteristics which differs significantly from the surrounding tissues. Therefore, in order to indicate the depth of penetration of the annulus fibrosus 4, identify the separation between the nucleus pulposus 3 and the annulus fibrosus 4, and to identify damage to the annulus fibrosus 4, the distal ends 8 of each probe can form part of the circuit of an electrical current impedance meter.

In addition to conducting electrical current as an electrode, and measuring electrical current impedance, the distal portions 8 of each probe 6 and 11 can alternatively include a resistive thermal unit to deliver heat energy to the annulus fibrosus 4.

The probes 6 and 11 can also include a temperature sensing device such as a thermometer, a thermistor, an optic fluorescent sensor, or thermocouple for providing additional monitoring and testing functions. For example, FIG. 7 shows a high frequency probe 6 inserted into a cannula with an insulated sleeve 13 and a bare metal tip 14 that contacts the tissues of the annulus fibrosus 4 and delivers electrical current at a radio frequency. The tip 14 of the probe 6 can also include a temperature sensor (not shown) to monitor the operation.

FIG. 8 illustrates an internal liquid cooled radio frequency electrode 6 with an insulated sleeve 13 to concentrate the delivery of electrical current. In this case, the probe 6 comprises a hollow tube of conductive metal, for example, with a sharp tip 15 and a liner tube 17 defining a central bore and an outer annular passageway. Cooling liquid passes down the central bore as indicated with arrows and is withdrawn to the outer annular passageway thereby cooling the tip 15. As such, the heat can be translated deeper into the tissue of the annulus fibrosus 4 without raising the temperature of the tissue immediately adjacent to the electrode 6.

FIG. 9 shows a similar probe with insulating sleeve 13 but with an extending remote reaching temperature sensor 16 deployed from the probe 6 once it is placed in its position. This sensor 16 allows monitoring of the temperature within the tissues at a distance remote from the probe surface 6.

FIG. 10 shows a probe 6 of similar configuration to that shown in FIG. 8 with internal liquid cooling. However, inner tube 17 defines one or more apertures close to the tip 15 which direct the flow of cooling liquid outward through the outer annular passageway. In this case, the inner tube 17 is made of a conductive material such as constantan and is welded to the outer tube 18 which is made of a different conductive material such as stainless steel. Therefore, the junction at the tip of the inner tube 17 and outer tube 18 acts as a thermocouple useful to measure temperature, in addition to providing flow channels for the flow of cooling liquid.

FIG. 11 shows another example of a probe 6 which has internal liquid cooling. An introducing catheter tube 5 has a sharp beveled end terminating in a point 19 useful to provide access to the annulus fibrosus 4 without risk of damage to the probe 6.

Figure 12:
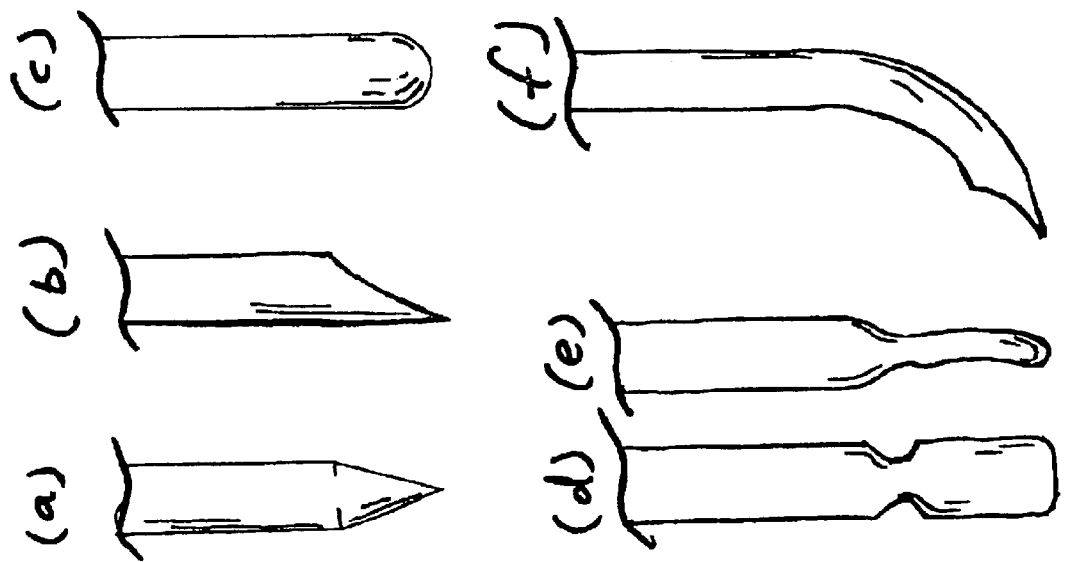
FIGS. 12(a) to 12(f) are views of various optional shapes that the distal end of the probe can adopt for placing the electrode tip in position.

FIG. 12a–12f shows different shapes which the distal end 8 of the probes 6 and 11 can adopt for insertion in the patient's body. FIG. 12A shows a pencil tip. FIG. 12B shows a sharp beveled tip. FIG. 12C shows a blunt end when cutting is not required. FIGS. 12D and 12E show front and side views of a spatula shaped tip whereas FIG. 12F shows a curved end tip with cutting bevel end. The different shapes can allow for the current to be directed into the annulus fibrosus in a profile corresponding to the shape of the tip, thereby controlling the current density which will in turn control the size and shape of the lesion.

Figure 13:
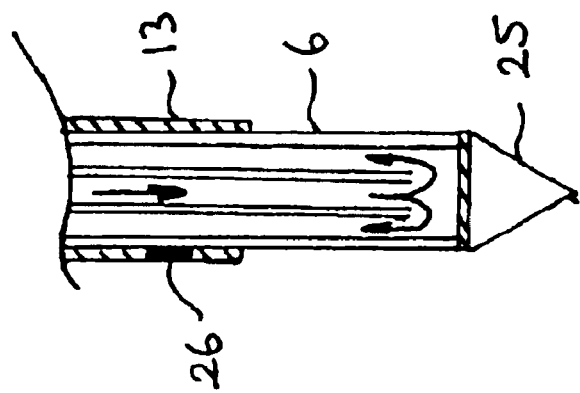
FIG. 13 is a view of a liquid-cooled electrode with an electrically isolated, impedance monitoring tip used to accurately position the energy delivery component in the annulus fibrosus.

FIG. 13 shows a further embodiment of the probes 6 and 11 in which the distal end 8 contains an impedance measuring tip 25. Impedance measuring tip 25 can be used to help determine the position of the electrode 6 while the probe is being inserted into the annulus fibrosus. Though not shown, probe 6 is connected to a power source including a control unit for regulating the power transmitted by tip 25. Impedance measuring tip 25 may be operated to send very small pulses of low power, high frequency current through the tissue to a dispersive ground electrode on the surface of the patient's skin (not shown). As the impedance measuring tip 25 is pushed through the annulus fibrosus the impedance can be measured. When the impedance measuring tip 25 touches the nucleus pulposus the impedance level will drop. This drop in impedance indicates that the distal end 8 is within the annulus fibrosus and not in the nucleus pulposus. FIG. 13 also illustrates a sleeve 13 having a temperature sensor 26 located at an outer end. By locating a temperature sensor 26 at this position the temperature of the tissue surrounding the sleeve 13 can be measured as is well understood by the person skilled in the art. The results may be advantageously compared to a temperature reading of the tissue taken at the distal end 8 as discussed previously. Alternatively, temperature sensors can be located within the central bore and the outer passageways of the cooling means illustrated in FIG. 8. By measuring the change in temperature of the inflow and outflow of cooling fluid the temperature of the tissue located adjacent the electrode can be determined. Other locations of the temperature sensors can also be used for comparison of tissue temperatures within the annulus fibrosus.

Figure 14:
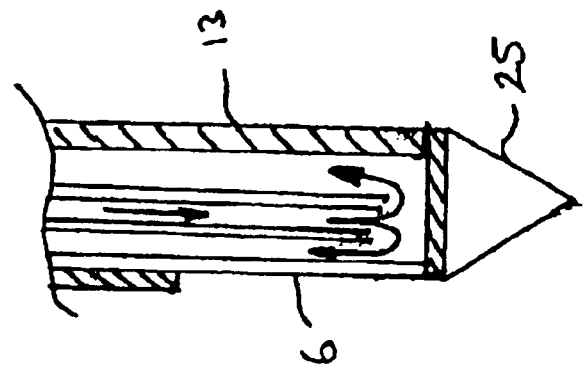
FIG. 14 is a similar view with the electrode on one side of the probe.

FIG. 14 shows a similar view of the distal end 8 of the probes 6 and 11 containing an impedance measuring tip 25 on the distal end 8. Sleeve 13 may be configured to predominantly expose one side of the distal end 8. By exposing the electrode 6 on one side, control of the direction of the lesion is increased. It will be understood to persons skilled in the art that the embodiments of the invention in which the probe has an impedance measuring tip will also include internal conduits to hold wires that connect the impedance measuring tip to the energy delivery and monitoring devices.

As will be further understood from the above description, the use of two probes does not overly complicate the surgical procedure since attaining percutaneous access to the disc from the posterolateral approach is a relatively simple and quick procedure. Because of problems associated with the positioning of prior art probes, it is sometimes necessary to perform a second insertion of a prior art probe which insertion is from the opposite side of the disc. The two probe approach of the present invention avoids the inaccurate positioning of the probe that may cause insufficient heating of the required region of the annulus fibrosus.

One advantage of utilizing two probes, as described in the present invention, is that a large elongate area of the annulus fibrosus can be treated in a focussed, controllable manner. Use of a single probe electrode requires a ground or second electrode attached to the skin surface of the patient to complete the circuit. The electrical current delivered by the single inserted probe in or adjacent to the annulus fibrosis delivers a concentrated current in the immediate area. The current is dissipated a short distance from the tip of the single probe, passes through the patient's body and is grounded by the second electrode attached to the skin surface. However, in the present invention, the second electrode is also positioned adjacent to or in the annulus fibrosus. Electrical current is passed between the closely positioned electrodes through the annulus fibrosus, which has an electrical impedance lower than the surrounding tissues. As a result, the electrical current passes directly through the annulus fibrosus with a low degree of dissipation between the two electrodes in a focussed or concentrated pattern. Preferably the electrical current is delivered at radio frequency, or at least above the physiological stimulus range for example above approximately 20 kilohertz. Since the electrical current does not dissipate as rapidly but passes directly between the closely positioned electrodes, the delivery of electrical current is more focussed and controllable to create a heated region for denervation and modulation of the annulus fibrosus in a more precisely selected area of the annulus fibrosus.

Additionally since the annulus fibrosus has a lower impedance to electrical current compared with the tissue surrounding the disc, the probes preferably include an impedance measurement device to accurately identify when the tip of the probe is inserted into the annulus fibrosus and to locate the border or margin between the annulus fibrosus and the nucleus pulposus. The impedance measurement gives an indication of the depth to which the probe is inserted into the annulus fibrosus. Further, impedance of electric current through the annulus fibrosus between the two electrodes varies depending on any physical damage to the annulus fibrosus. For example fissures or cracks, delamination or escape of nucleus pulposus material through the annulus fibrosus all effect the impedance of electrical current. As a result, therefore measuring impedance between the two probes or at the tip of a single probe can be used to identify and locate damaged areas of the annulus fibrosis. This information can be used to better understand the pathology of the particular intervertebral disc being treated. It can also be used to determine the power and duration of current application in order to optimally heat the disc.

Another advantage of the invention is that the probes need not enter in to the nucleus pulposus to target treatment of the posterior region of the annulus fibrosus. As discussed above, applying heat or electrical current energy to the nucleus pulposus can effect the metabolism of the nucleus pulposus, damage enzymes and nutrition capacity, and effect cartilage endplates detrimentally. The present invention targets the posterior region of the annulus fibrosus without unnecessarily affecting the nucleus pulposus, cartilage endplates and anterior annulus fibrosus. As discussed, in one embodiment of the invention each probe comprises an impedance-monitoring tip at the very distal end that is electrically isolated from the electrode and communicates between the tip and a dispersive grounding electrode on the surface of the body. As the probe is inserted into the annulus fibrosus the impedance is monitored to indicate the position in relation to the inner wall of the annulus fibrosus. Additionally, depth markers (not shown) can be used on the elongate probe which will also help to determine the depth that the distal end of the probe is inserted past the outer end of the introducer. Another additional step that can be used to ensure the electrode is positioned properly in the annulus fibrosus is to inject a small amount of radiopaque contrast solution into the nucleus pulposus just inside the inner wall so the inner wall could be visualized with fluoroscopy.

Use of dual electrode probes also provides improved access to critical areas of the annulus fibrosus. A major proportion of all disc injuries occurs in the posterior area. Proper access to deliver heat or electrical energy to the posterior portion of the annulus fibrosus is considered essential. However, access to the posterior disc area by probes is very limited, as will be apparent to those skilled in the art, with a very small window of access due to the nerves and bones adjacent to the disc area. The invention solves this difficulty by permitting two probes to access through the conventional posterolateral path to the disc at opposite sides of the posterior annulus fibrosus without piercing the nucleus pulposus. Passing electrical current between the tips of the two probes provides treatment for the posterior area of the annulus fibrosus by directing current through the annulus fibrosus between the two probes. Radio frequency electrical current, microwave, ultrasound or resistive thermal energy can be passed between both probes to modulate the collagen and denervate nociceptors in the periphery of the disc, between the probes.

As discussed, the probes may additionally include active shape control mechanisms to develop the trajectory of the probe tip as it is driven through the annulus fibrosus. Such active shape controlling means include cables for a mechanical actuator, hydraulic or piezo-electric devices and solenoids as known to persons skilled in the art.

The probes can also include a cooling mechanism that removes heat from the electrodes. This allows heat to be deposited in the annulus fibrosus further away from the electrode surfaces while keeping the temperature of the tissue immediately adjacent the electrodes relatively low. Without a cooling mechanism, the maximum temperature would be in the tissue immediately adjacent the electrodes, where the current density is greatest. Tissue temperature would decline as the distance from the electrodes increases. The advantage of including an electrode cooling mechanism is that the maximum temperature would be in the tissue several millimeters from the electrodes. Therefore, a greater power could be used that would increase the temperature at a greater distance from the electrodes and the temperature of the tissue heated would be more uniform. A further advantage is that it would take less time to heat the treatment segment if greater power is used with a cooled probe. A further advantage of including a cooling mechanism is the ability to deposit heat further from the electrodes without the risk of overheating the tissue immediately adjacent the electrodes. Overheating tissue can have a negative effect on the therapy and in extreme cases can char the tissue inhibiting healing of the perforation made by inserting the electrode in to the annulus fibrosus. The preferred mechanism of cooling the electrodes includes a contained flow of cooling fluid, such as water, through an internal lumen of the electrode. Other methods of cooling include the use of other liquids such as cooled water or liquid nitrogen, expansion of compressed gas, or thermoelectric cooling.

The invention could also be used to apply high frequency current to the annulus fibrosus without raising the temperature above 42° C. This can be achieved in a number of ways including using a modified signal wave, using a continuous wave with decreased power and/or duration of application, using an electrode cooling mechanism, or a combination thereof.

In use, first and second intradiscal lesioning probes, as described above, are inserted into the annulus fibrosus. Each probe has an energy delivery means located at a distal end thereof. The distal ends are spaced apart when inserted and energy is delivered from an energy source connected to the probes through the energy delivery means to the annulus fibrosus. Additionally the use of the probes can include measuring the impedance between the energy delivery means of the probes via an impedance monitor connected to the probes and delivering the energy in response to the measured impedance.

The insertion of the probes can be aided by the use of first and second elongate introducer tubes, as illustrated and described above, where each introducer tube has an inner end, an outer end and a longitudinal bore extending between the ends. The introducer tubes are inserted into the annulus fibrosus thereby providing external surgical access to two spaced apart treatment sites of the annulus fibrosus through the bores. The probes are then inserted through the first and second introducer tubes respectively. Preferably, each probe slidably engages and flexibly conforms to the bore when inserted. The introducer tube may have a temperature sensor near the outer end for measuring the tissue surrounding the end when the introducer tube is inserted. The use of an additional temperature sensor on the tube can assist in the user comparing the tissue located at a distance from the energy delivery means with the temperature of the tissue located adjacent the energy delivery means.

The device of the present invention is useful to treat discogenic pain, degenerative intervertebral discs, and morphological abnormalities of the intervertebral disc. Moreover, the device is useful to strengthen the annulus fibrosus, shrink annular fissures and impede them from progressing, cauterize granulation tissue in annular fissures and denaturing pain-causing enzymes in nucleus pulposus tissue that has migrated to annular fissures. Additionally, the device may be operated to treat a bulging disc with a minimally invasive technique that delivers sufficient energy to the annulus fibrosus to breakdown or cause a change in function of selective nerve structures in the intervertebral disc, modify collagen fibrils with predictable accuracy, and to accurately reduce the volume of intervertebral disc tissue.

Although the above description relates to specific embodiments as presently contemplated by the inventors, it will be understood that the invention in its broad aspect includes mechanical and functional equivalents of the elements described herein.

We claim:

1. A method for treatment of an intervertebral disc, the disc comprising a nucleus pulposus and an annulus fibrosus, said method comprising the steps of:

i) inserting a first and a second probe to respective spaced apart treatment sites for annulus fibrosus, each probe having an energy delivery means located at a distal end thereof, the distal ends being inserted to the treatment sites; and ii) delivering energy from an energy source through the energy delivery means such that said energy is focused between said energy delivery means.

2. The method as claimed in claim 1 comprising a step of measuring impedance between the energy delivery means of the probes and delivering the energy in response to the measured impedance.

3. The method as claimed in claim 1, comprising a step of cooling the energy delivery means of at least one of the probes with a cooling means provided to said at least one of the probes.

4. The method as claimed in claim 3 wherein said cooling means comprises at least one of a contained flow of cooling fluid, expansion of compressed gas and thermoelectric cooling.

5. The method as claimed in claim 1 wherein the step of inserting, comprises inserting at least one of the probes through an introducer tube that is inserted to one of the treatment sites.

6. The method as claimed in claim 5 comprising inserting said at least one of the probes to slidably engage a bore of said introducer tube.

7. The method as claimed in claim 5 comprising determining a position of the distal end of the probe relative to said introducer tube.

8. The method as claimed in claim 1 comprising a step of measuring at least one of a temperature of a tissue located adjacent to said energy delivery means and a temperature of a tissue located at a distance from said energy delivery means.

9. The method as claimed in claim 8, wherein temperature is measured using a temperature measuring device that is at least one of a thermistor, a thermocouple, a thermometer and an optic fluorescent sensor.

10. The method as claimed in claim 1 wherein the step of delivering energy comprises delivering energy sufficient to cause a change in function of nerve structures in said intervertebral disc.

11. The method as claimed in claim 1 wherein the step of delivering energy comprises delivering energy sufficient to modulate collagen.

12. The method as claimed in claim 1 wherein the step of delivering energy comprises delivering energy sufficient to denature pain-causing enzymes.

13. The method as claimed in claim 1 wherein said energy is at least one of radiofrequency energy, microwave energy, thermal energy and ultrasonic energy.

14. The method as claimed in claim 1 wherein the step of delivering energy comprises delivering energy without raising the temperature of said annulus fibrosus above 42° C.

15. The method as claimed in claim 14 wherein said energy is delivered as a modified signal wave.

16. The method as claimed in claim 1 comprising a step of measuring impedance at the distal end of at least one of the probes and determining at least one of:

a location of a tip of said distal end of at least one probe in said intervertebral disc;

a separation between said nucleus pulposus and said annulus fibrosus;

an identity and location of damage in said annulus fibrosus; and a pathology of said intervertebral disc.

17. The method as claimed in claim 1 comprising a step of injecting radiopaque contrast solution into said nucleus pulposus.

18. The method as claimed in claim 1 comprising a step of controlling a shape of a tip of at least one of the probes using an active shape controlling means.

19. The method as claimed in claim 18 wherein said active shape controlling means is at least one of a hydraulic device, a piezo-electric device, at least one solenoid and a mechanical actuator.

20. The method as claimed in claim 1 comprising inserting said distal ends partially into said annulus fibrosus.

* * * * *